United States Patent [19]
Gruber et al.

[11] Patent Number: 5,817,640
[45] Date of Patent: Oct. 6, 1998

[54] METHODS OF PREVENTING TISSUE DAMAGE ASSOCIATED WITH DECREASED BLOOD FLOW BY ADMINISTRATION OF AICA RIBOSIDE COMPOUNDS

[75] Inventors: Harry E. Gruber, Rancho Santa Fe; Kevin M. Mullane, Del Mar; Paul K. Laikind, San Diego, all of Calif.

[73] Assignee: Gensia Pharmaceuticals, San Diego, Calif.

[21] Appl. No.: 443,245

[22] Filed: May 16, 1995

Related U.S. Application Data

[63] Continuation of Ser. No. 296,266, Aug. 25, 1994, abandoned, which is a continuation of Ser. No. 949,101, Sep. 21, 1992, abandoned, which is a continuation-in-part of Ser. No. 770,023, Sep. 30, 1991, abandoned.

[51] Int. Cl.$^6$ ................................................. A61K 31/70
[52] U.S. Cl. .............................. 514/46; 514/45; 514/821; 514/822; 514/824; 514/885; 514/886; 435/975
[58] Field of Search ............................... 514/45, 46, 821, 514/822, 824, 861, 885, 886; 435/975

[56] References Cited

U.S. PATENT DOCUMENTS

| | | |
|---|---|---|
| 4,575,498 | 3/1986 | Holmes et al. . |
| 4,912,092 | 3/1990 | Gruber . |
| 5,008,251 | 4/1991 | Gruber . |
| 5,030,623 | 7/1991 | Gruber . |
| 5,118,601 | 6/1992 | Gruber . |
| 5,187,162 | 2/1993 | Gruber et al. . |
| 5,731,432 | 3/1998 | Erion et al. . |

*Primary Examiner*—James O. Wilson
*Attorney, Agent, or Firm*—Lyon & Lyon LLP

[57] ABSTRACT

Methods of preventing tissue damage associated with decreased blood flow in a human by administering AICA riboside or a prodrug thereof in an amount which provides a blood plasma concentration of between 1 μg/ml and 20 μg/ml of AICA riboside for a time sufficient to reduce the risk of said tissue damage in said human. Methods of preventing an adverse clinical outcome, such as an adverse cardiovascular and/or cerebrovascular event, in a patient at risk for such outcome by administering AICA riboside or a prodrug thereof in an amount which provides a blood plasma concentration of between 1 μg/ml and 20 μg/ml of AICA riboside for a time sufficient to reduce the risk for said patient.

52 Claims, 3 Drawing Sheets

METHODS OF PREVENTING TISSUE DAMAGE ASSOCIATED WITH DECREASED BLOOD FLOW BY ADMINISTRATION OF AICA RIBOSIDE COMPOUNDS

This application is a continuation of application Ser. No. 08/296,266, filed Aug. 25, 1994, now abandoned, which is a continuation of application Ser. No. 07/949,101, filed Sep. 21, 1992, now abandoned, which is a continuation-in-part of U.S. application Ser. No. 07/770,023, filed Sep. 30, 1991, now abandoned which is fully incorporated herein by this reference.

FIELD OF THE INVENTION

This invention relates to administration of AICA riboside compounds to prevent tissue damage associated with decreased blood flow in humans and/or to prevent adverse clinical outcomes in patients at risk for such outcomes.

BACKGROUND OF THE INVENTION

Gruber (U.S. Pat. No. 4,912,092) described prophylactic administration of AICA riboside compounds, including analogs and prodrugs thereof, to prevent tissue damage associated with undesired decreased blood flow. The AICA riboside compounds are administered in amounts between 0.1 and 500 mg/kg/day. AICA riboside's prodrugs, including those set forth in the commonly assigned U.S. Pat. No. 5,082,829, entitled "AICA Riboside Prodrugs," U.S. application Ser. No. 07/408,107, filed Sep. 15, 1989, entitled "Methods and Compounds for AICA Riboside Delivery and for Lowering Blood Glucose," and U.S. application Ser. No. 07/466,979, filed Jan. 18, 1990, entitled "Method and Compounds for AICA Riboside Delivery and for Lowering Blood Glucose," all of which are incorporated herein in their entireties by this reference, may also be administered. Certain prodrugs of AICA riboside are defined therein, and generally are compounds which, when introduced into the body, will metabolize into AICA riboside or an active metabolite, for example, AICA riboside monophosphate. Other prodrugs include mono-, di- and tri-5' phosphates of AICA riboside.

SUMMARY OF THE INVENTION

Applicant's invention relates to the discovery of particularly therapeutic concentrations of AICA riboside for the prevention of tissue damage associated with decreased blood flow in humans, and the determination of dosages which achieve efficacy while avoiding undesirable side effects. Applicant's invention also relates to the discovery of particularly therapeutic concentrations and dosages of AICA riboside which prevent or reduce the severity of adverse clinical outcomes, including adverse cardiovascular and/or cerebrovascular events in patients at risk for such events. Applicant has discovered that it is preferable to maintain an intravascular concentration of AICA riboside of from about 1 μg/ml to about 20 μg/ml, to obtain the beneficial effects of AICA riboside, and to prevent side effects which may occur at higher dosages. Applicant has discovered that the ideal range is about 3 to about 6 μg/ml, and especially about 5 μg/ml.

Thus, in a first aspect, the invention features a method of preventing tissue damage associated with decreased blood flow in humans by administering AICA riboside to a person in an amount, which maintains a blood plasma concentration of AICA riboside for a sufficient time so that the risk of such tissue damage is reduced in that person, of from about 1 μg/ml to about 20 μg/ml, preferably a concentration of about 3 μg/ml to about 6 μg/ml, and more preferably at about 5 μg/ml. It is desirable that the concentration of AICA riboside in the person results in an elevation of serum uric acid to a level of no greater than about 16.0 mg/dl, and more preferably no greater than about 9.0 mg/dl.

By "preventing tissue damage" is meant lessening the frequency, duration and/or severity of ischemic events and/or reducing the deleterious effects of undesired decreased blood flow on the tissue. The incidence, duration and severity of ischemic events may be measured by methods known in the art. For example, in the use of AICA riboside during coronary artery bypass graft (CABG) surgery, the following methods may be employed: (1) comparison of ST segment changes on continuous Holter electrocardiographic recordings; (2) assessment of regional wall motion by transesophageal echocardiography; (3) serial measurement of creatinine phosphokinase MB; and (4) serial 12-lead electrocardiographic analyses. Methods for measurement of deleterious effects of undesired decreased blood flow are also known in the art. Deleterious effects of tissue damage may include adverse clinical outcomes, such as adverse cardiovascular and/or cerebrovascular events including those observed in connection with CABG surgery. Such adverse events include cardiac death (i.e., death due to primarily a heart-related cause), transmural and/or non-transmural myocardial infarction, cerebrovascular accident, congestive heart failure, and life-threatening dysrhythmia, which may occur during and/or following such surgery. Other adverse clinical outcomes which may be prevented by administration of AICA riboside include hepatic injury (documented by enzyme elevation), pancreatic injury (documented by enzyme elevation), disseminated intravascular coagulation (including that due to bowel ischemia) and death (from non-cardiac causes). By reducing the risk of tissue damage is meant diminishing the opportunity for tissue damage as compared to the opportunity which existed without the administration of AICA riboside. The use of AICA riboside or prodrugs thereof may also protect brain tissue from injury due to decreased blood flow.

By AICA riboside is meant 5-amino-1-β-D-ribofuranosyl-imidazole-4-carboxamide (also known as acadesine).

In a second aspect, the invention features a method of preventing tissue damage associated with decreased blood flow in humans by administering AICA riboside for a sufficient time to reduce the risk of such tissue damage, in a dosage of from about 0.01 mg/kg/min to about 2.0 mg/kg/min; preferably, from about 0.05 mg/kg/min to about 0.2 mg/kg/min; and more preferably of about 0.1 mg/kg/min for anesthetized patients and about 0.125 mg/kg/min for non-anesthetized patients or those patients anesthetized for a short period of time.

In certain embodiments, the tissue to which damage is prevented is cardiac muscle or cardiac microvasculature. In other embodiments, the tissue to which damage is prevented is brain tissue or brain microvasculature.

In certain embodiments, the tissue damage which is prevented is that tissue damage which occurs as a result of undesired decreased blood flow occurring during surgery, such as during cardiac surgery (for example, CABG surgery) or during vascular surgery. In these embodiments, the compound may be administered beginning shortly before the induction of anesthesia, and continue through the duration of the surgery, and for about one hour following completion of surgery, or for at least about seven hours following completion of surgery, or longer, depending on factors such as duration of the surgery.

In another embodiment, the AICA riboside is administered both to a patient undergoing cardiac surgery and in the perfusate solution used to perfuse the patient's heart during such surgery. Preferably, the AICA riboside concentration in the perfusate solution is in the range of about 5 μM to about 100 μM, more preferably about 20 μM.

In another embodiment, AICA riboside is administered in combination or conjunction with allopurinol, preferably in an amount of between about 100 mg/day to about 1200 mg/day, and more preferably in an amount of about 300 mg/day. Allopurinol reduces uric acid levels and thus, may be administered in combination with, or in conjunction with, AICA riboside (or a prodrug of AICA riboside) to allow administration of a larger dosage of AICA riboside or prodrug while avoiding adverse side effects of increased uric acid levels. As noted above, it is desirable for uric acid levels not to exceed about 16 mg/dl, and preferable for them not to exceed about 9 mg/dl.

In another embodiment, the invention further involves the identification of a person in need of prevention of such decreased blood flow, prior to administering AICA riboside (or a prodrug thereof). Those skilled in the art will recognize that by "identification" is meant determination of patients at risk for tissue damage, e.g., those patients undergoing surgery or other procedures. Risk factors for those patients undergoing cardiac surgery include elevated age (for example, above 70 years of age); emergency or urgent surgery, which may be complicated by unstable angina; failed percutaneous transluminal coronary angioplasty; decreased left ventricular function (as determined by an ejection fraction of less than about 40%); chronic or acute renal failure; dysrhythmia (under treatment); or MI within the past several years. See, e.g., Mangano, *Anesthesiology* 72:153–184 (1990). Risk factors for those patients undergoing non-cardiac surgery include elevated age (for example, above 65–70 years of age); atherosclerotic heart disease, i.e., coronary artery disease, as evidenced by peripheral vascular disease or carotid artery disease; diabetes; renal failure; heart failure currently under therapy; left ventricular hypertrophy and hypertension; hypertension for over 5 years; emergency or urgent surgery; MI within 6 months to a year prior to surgery; angina; arrhythmia or hypercholesterolemia. The invention also includes identification of patients who are in need of prophylactic administration of AICA riboside because of a chronic, genetic, or similar condition, or due to angina, transient ischemic attack, evolving or recent MI, or evolving or recent stroke. Thus, those not undergoing surgery may face an increased risk for tissue damage, as well.

In another aspect, the invention features a method of preventing tissue damage associated with decreased blood flow in a human by administering a total dose of AICA riboside in an amount of from 10 mg/kg to 200 mg/kg; preferably in an amount between 30 mg/kg and 160 mg/kg. For cardiac surgery, a preferred amount is about 40 mg/kg. For other indications, such as non-cardiac surgery, a preferred amount is about 120 mg/kg. Those skilled in the art will recognize that such total doses can be achieved by varying the concentration of AICA riboside administered, the rate of administration and/or the duration of administration.

In another aspect, the invention features a method of prevention of tissue damage associated with undesired decreased blood flow in humans by administering a prodrug of AICA riboside in an amount effective to provide a blood plasma level of AICA riboside from about 1 μg/ml to about 20 μg/ml, preferably about 3 μg/ml to about 6 μ/ml and more preferably about 5 μg/ml. The amount of prodrug necessary to achieve these levels is readily determined by one skilled in the art using standard methodologies. A prodrug may be administered in combination with, or in conjunction with, allopurinol, preferably with allopurinol being administered in an amount of from about 100 mg/day to about 1200 mg/day, and preferably in an amount of about 300 mg/day. Such administration will avoid adverse side effects of high uric acid levels. A prodrug may be administered as described above for AICA riboside itself.

In another aspect, the invention features a method of preventing adverse clinical outcomes, including adverse cardiovascular and/or cerebrovascular events, in those at risk for such outcomes, which comprises administering AICA riboside, or a prodrug thereof, in an amount which provides a blood plasma concentration of AICA riboside of between about 1 μg/ml and about 20 μg/ml, preferably between about 3 μg/ml and about 6 μg/ml and more preferably about 5 μg/ml. By "adverse clinical outcome" is meant an event which has a clinically detrimental effect on a patient. By "adverse cardiovascular event" is meant an event pertaining to the heart or blood vessels which is detrimental to a patient. By "adverse cerebrovascular event" is meant an event pertaining to blood vessels affecting the brain which is detrimental to a patient.

The invention further involves the identification of patients at risk for adverse clinical outcomes, including adverse cardiovascular and adverse cerebrovascular events. Risk factors for those patients undergoing cardiac surgery include elevated age (for example, above 70 years of age); emergency or urgent surgery, which may be complicated by unstable angina; failed percutaneous transluminal coronary angioplasty; decreased left ventricular function (as determined by an ejection fraction of less than about 40%); chronic or acute renal failure; dysrhythmia (under treatment); or MI within the past several years. See, e.g., Mangano, *Anesthesiology* 72:153–184 (1990). Risk factors for those patients undergoing non-cardiac surgery include elevated age (for example, above 65–70 years of age); atherosclerotic heart disease, i.e., coronary artery disease, as evidenced by peripheral vascular disease or carotid artery disease; diabetes; renal failure; heart failure under therapy; left ventricular hypertrophy and hypertension; hypertension for over 5 years; emergency or urgent surgery; MI within 6 months to a year prior to surgery; angina; arrhythmia or hypercholesterolemia. The invention also includes identification of patients who are in need of prophylactic administration of AICA riboside because of a chronic, genetic, or similar condition, or due to angina, transient ischemic attack, evolving or recent MI, or evolving or recent stroke. Thus, those not undergoing surgery may face an increased risk for tissue damage, as well.

In another aspect, the invention features a method of preventing adverse clinical outcomes, including adverse cardiovascular and/or cerebrovascular events in those at risk for such events by administering AICA riboside for a sufficient time to reduce the risk of such events, in a dosage of from about 0.01 mg/kg/min to about 2.0 mg/kg/min; preferably from about 0.05 mg/kg/min to about 0.2 mg/kg/min; and more preferably of about 0.1 mg/kg/min or 0.125 mg/kg/min, depending on anesthesia.

In certain embodiments, the adverse cardiovascular event which is prevented is myocardial infarction. "Myocardial infarction" includes transmural and non-transmural myocardial infarction. In the case of CABG surgery, transmural MI is evidenced by the presence of a new Q wave in ECG testing and an elevated CK-MB concentration, and non-transmural MI is evidenced by elevated CK-MB concentration without a new Q wave. In other embodiments, the cardiovascular event which is prevented is cardiac death. By "cardiac death" is meant death of a patient from a primary cardiac cause, for example, from myocardial infarction, dysrhythmia or ventricle dysfunction.

In certain embodiments, the cerebrovascular event which is prevented is cerebrovascular accident. By "cerebrovascular accident" is meant injury to the brain associated with decreased blood flow, e.g., stroke.

In certain embodiments, the risk for adverse cardiovascular or cerebrovascular event occurs as a result of indications such as angina or transient ischemic attack. In other embodiments, the risk of adverse cardiovascular or cerebrovascular events occurs as a result of cardiac surgery, for example, CABG surgery, or as a result of non-cardiac surgery, for example, vascular surgery. In the case of surgery, the AICA riboside may be administered beginning shortly before the induction of anesthesia, and continued through the duration of surgery, for about 1 hour following completion of surgery, or for about 7 hours total. Administration may continue for a longer time, for example, 24 hours or more following surgery. Prolonged administration is especially effective for non-cardiac surgery because adverse events tend to occur later. For example, it has been observed that in cardiac surgery, MI tends to occur mainly in the first day following surgery, however, in non-cardiac surgery, MI tends to occur mainly in the second or third day following surgery. Thus, in the case of non-cardiac surgery, AICA riboside (or a prodrug) is administered for a more prolonged period after surgery, for example, for 7–48 hours.

In another embodiment, the AICA riboside is administered both to a patient undergoing cardiac surgery, and in the perfusate solution used to perfuse the patient's heart during such surgery. Preferably, the AICA riboside concentration in the perfusate solution is in the range of about 5 $\mu$M to about 100 $\mu$M, more preferably about 20 $\mu$M.

In another embodiment, AICA riboside is administered in combination or conjunction with allopurinol, preferably in an amount of between about 100 mg/day and about 1200 mg/day, and more preferably in an amount of between about 300 mg/day.

In another embodiment, the invention provides a method for preventing or reducing the occurrence of an adverse cardiovascular or cerebrovascular event in a patient undergoing CABG surgery, which method comprises the steps of: (a) administering to said patient 0.1 mg/kg/min AICA riboside intravenously for about 7 hours perioperatively; and (b) perfusing the heart of said patient with a perfusate solution of 20 $\mu$M AICA riboside.

In another aspect, the invention features a method of preventing, or reducing the severity of, myocardial infarction in a human at risk for myocardial infarction, which method comprises administering AICA riboside or a prodrug thereof to said human in an amount which provides a blood plasma concentration of AICA riboside in said human of between about 3 $\mu$g/ml and about 6 $\mu$g/ml, for a sufficient time to reduce the risk of said myocardial infarction. Increased risk of myocardial infarction may result from surgery, either cardiac surgery, such as CABG surgery, or non-cardiac surgery, such as vascular surgery, or from factors other than surgery, e.g., indications of reversible ischemia, such as angina or silent ischemia, or of evolving or recent MI or stroke.

In another aspect, the invention features a method of preventing, or reducing the severity of, cerebrovascular accident in a human at risk for cerebrovascular accident, which method comprises administering AICA riboside or a prodrug thereof to said human in an amount which provides a blood plasma concentration of AICA riboside in said human of between about 3 $\mu$g/ml and about 6 $\mu$g/ml, for a sufficient time to reduce the risk of said cerebrovascular accident. Increased risk of cerebrovascular accident may result from surgery, either cardiac (such as CABG surgery) or non-cardiac (such as vascular surgery) or from non-surgical risks such as transient ischemic attack.

In another embodiment, the invention features a method of preventing, or reducing the severity of, cardiac death, which method comprises administering AICA riboside or a prodrug thereof to said human in an amount which provides a blood plasma concentration of AICA riboside in said human of between about 3 $\mu$g/ml and about 6 $\mu$g/ml, preferably about 5 mg/ml, for a sufficient time to reduce the risk of said cardiac death. Increased risk of cardiac death may result from the surgery, cardiac or non-cardiac. For example, the risk may result from CABG surgery.

The AICA riboside may be administered continuously or in a plurality of doses. To reduce the risk of tissue damage, the AICA riboside may be administered for a period of at least about 15 minutes. It may be administered for a duration of greater than about 4 hours and preferably for a duration of about 7 hours. In other cases, the AICA riboside may be administered for a duration of greater than about 10, 12, 16, 24, or even about 48 hours.

The AICA riboside may be administered intravenously, by intracoronary or intraarterial infusion, orally, or by any other methods known in the art, including introduction into the patient's blood in an extracorporeal circuit, for example, using a heart-lung machine or dialysis. AICA riboside may be administered prophylactically, or in response to a known bodily condition.

In one embodiment, AICA riboside is prepared as a therapeutic solution from a lyophilized form to prevent variable discoloration of a liquid formulation observable during storage. Preferably, the AICA riboside is non-pyrogenic.

In another aspect, the invention features a kit for use in administering AICA riboside to a patient undergoing cardiac surgery, e.g., CABG surgery, which comprises lyophilized AICA riboside for use in preparing an AICA riboside solution for intravenous infusion into a patient undergoing cardiac surgery and AICA riboside in solution for use in preparing a cardioplegic perfusate solution to be used to perfuse the heart of a patient undergoing cardiac surgery. Preferably, the AICA riboside is non-pyrogenic. Preferably, the lyophilized AICA riboside is provided in an amount of from 100 mg to 2,000 mg; more preferably in an amount of 500 mg. Preferably, the AICA riboside in solution is provided in a volume of from 1 ml to 20 ml; more preferably 5 ml. Preferably, the concentration of the AICA riboside in solution is about 1 mg/ml.

The lyophilized AICA riboside may be combined with a suitable diluent, such as water or saline solution to put it in a form suitable for infusion into the patient.

The AICA riboside in solution may be in a solution of water, saline solution, or cardioplegic solution. The AICA riboside in solution is of a concentration suitable for adding to cardioplegic perfusate solution such that the final concentration of AICA riboside in the cardioplegic solution is from 5 $\mu$M to 100 $\mu$M, preferably 20 $\mu$M. For example, if 5 ml of 1 mg/ml AICA riboside is added to one liter of cardioplegic perfusate solution, the resulting concentrate will be approximately 5 $\mu$g/ml or 20 $\mu$M.

One of the advantages of applicant's discovery of the particularly useful therapeutic concentrations and dosages of AICA riboside is that efficacy can be obtained at dosages at which the side effects of elevated serum or urinary uric acid levels and/or crystalluria are lessened, if not avoided altogether, and which avoid decreased blood glucose levels.

Applicant also discovered that lower doses of AICA riboside were needed to achieve the desired blood concentration levels in anesthetized patients than in non-anesthetized patients. It appears that the dose needed in anesthetized patients may be about 20–50% less than the dose needed in non-anesthetized patients. Thus, a preferred dosage of AICA riboside (or prodrug) in a non-anesthetized patient or a patient anesthetized for a short time is larger than the preferred dosage for an anesthetized patient. Accordingly, dosages of from about 0.075 mg/kg/min to about 0.30 mg/kg/min are preferred in such cases, more preferably between about 0.10 mg/kg/min and about 0.15 mg/kg/min, and most preferably about 0.125 mg/kg/min.

Other features and advantages of the invention will be apparent from the following description of the preferred embodiments and from the claims.

DESCRIPTION OF PREFERRED EMBODIMENTS

The drawings will first briefly be described.

DRAWINGS

DETAILED DESCRIPTION

By the following experiments, applicant has determined the concentrations and dosages of AICA riboside which decrease the frequency, duration and severity of ischemic events and which decrease tissue damage, while avoiding side effects such as clinically significant elevated serum and urinary uric acid levels and crystalluria. Applicant has also determined the concentrations and dosages of AICA riboside which prevent or reduce the severity of adverse clinical outcomes, such as adverse cardiovascular and cerebrovascular events.

The following Examples are not limiting to the invention. Those in the art will recognize that administration of AICA riboside in the stated amounts will reduce tissue damage resulting from decreased blood flow, and will reduce the incidence of adverse clinical outcomes, such as adverse cardiovascular and cerebrovascular events, in instances other than CABG surgery, as well.

EXAMPLE 1

EFFECTS OF AICA RIBOSIDE IN PATIENTS UNDERGOING CORONARY ARTERY BYPASS GRAFT (CABG) SURGERY: PHASE 2 CLINICAL TRIALS

These experiments were undertaken to assess the effects of AICA riboside on the frequency, duration, and severity of cardiac ischemic events and left ventricular function during and following CABG surgery. The effect of AICA riboside treatment on difficulty in weaning from cardiopulmonary bypass was also assessed. In addition, the effect of AICA riboside on the incidence of certain adverse clinic outcomes was evaluated.

Study Design

The study was a multi-center randomized double blind multi-dose placebo controlled parallel group study which evaluated 118 patients in four centers. Patients scheduled for non-emergency CABG surgery were randomly allocated to treatment with one of two doses of AICA riboside, or placebo, by continuous infusion throughout the procedure. Clinical outcomes, hemo-dynamics and the occurrence and severity of ischemia (by continuous electrocardiography (ECG) and transesophageal echocardiography (TEE)) were recorded and compared between treatment groups.

Patients

Included in the study were females not of child-bearing potential and males who were at least 30 years old and who were scheduled to have non-emergency CABG surgery for the treatment of coronary artery disease confirmed by typical changes (at least 50% stenosis of 2 or more major vessels) as shown by coronary angiography carried out within a six-month period prior to surgery. Patients with unstable angina were included, provided that the patient had been stable for at least 24 hours and that myocardial infarction had not occurred within the previous 2 weeks. Excluded from the study were patients undergoing emergency CABG or repeat CABG; those with resting ejection fraction less than 30%, cardiac index less than 1.5 L/min/m$^2$, or with idiopathic cardiomyopathy, significant valvular disease, severe left ventricular hypertrophy, or major intraventricular conduction abnormalities. Also excluded were patients with insulin dependent diabetes mellitus or hypoglycemic states, hepatic or renal disease, uncontrolled gout or a recent history of alcohol or other drug abuse. Thrombolytic therapy was prohibited within the 2 weeks prior to surgery, amiodarone for 60 days and dipyridamole, theophylline and aminophylline for 24 hours before the study. Smoking and ingestion of any methylxanthine-containing foods or drinks were prohibited from 12 hours before drug administration until discharge from the intensive care unit.

Treatment and Methods

Patients scheduled for CABG surgery and selected as described above were randomly allocated to receive an infusion of AICA riboside (0.19 mg/kg/min or 0.38 mg/kg/min initially; 0.05 mg/kg/min or 0.1 mg/kg/min after the first six patients) or placebo commencing shortly before induction of anesthesia and continuing for 7 hours; in all cases this meant that the infusion was not terminated until surgery had been completed and the patient was recovering in the intensive care unit. AICA riboside (20 $\mu$M final concentration) or placebo was also added to the crystalloid cardioplegic solution used to perfuse the coronary circulation during the bypass period. No other drugs were added to the crystalloid cardioplegic solution.

During the pre-operative period, a routine history, a physical examination, laboratory determinations, an electrocardiogram (ECG) and a chest x-ray were obtained. A continuous ECG (Holter) recording for a minimum of 8 hours before intubation was obtained. Routine cardiovascular medications were continued up to the morning of surgery as indicated. Immediately before surgery commenced, a catheter was placed in the radial artery for blood pressure measurements and arterial blood sampling. A triple lumen thermodilution catheter was introduced into the pulmonary artery for hemodynamic measurements. After tracheal intubation, an echocardiographic transducer was positioned at the level of the mid-papillary muscles using the transesophageal approach.

During surgery, anesthesia was maintained by continuous infusion of fentanyl and midazolam. Routine clinical parameters were recorded using standard operating room monitoring equipment. Continuous 2-lead Holter ECG and TEE data were recorded. Standard surgical procedures (e.g., aorta cross-clamping, crystalloid cardioplegia, cardio-pulmonary bypass, hypothermia) were used. Anastomoses were constructed, aorta cross-clamp removed and patients were discontinued from bypass when body temperature was 37° C. The quality of anastomosis was judged by the surgeon. Difficulty in weaning from bypass was judged by need for one or more of the following: pacemaker, return to bypass, balloon pump or vasopressor administration. Hemodynamic measurements, including heart rate, arterial blood pressure, pulmonary capillary wedge pressure and cardiac output, were recorded before sternotomy, 15 and 30 min after bypass and upon chest closure. Radial artery and pulmonary artery pressures, myocardial and whole body temperature, $O_2$ saturation, end-tidal $CO_2$ and arterial blood gases were measured, and ECG recordings were obtained as clinically indicated. Hemodynamic variables (blood pressure, heart rate, pulmonary capillary wedge pressure) were controlled within 20% of baseline using prescribed regimens.

During the post-operative period through the first post-operative day, morphine and midazolam were used for sedation and analgesia. The cardiovascular medications required were recorded. During this period, continuous ECG monitoring (Holter) was performed for up to 48 hours. Hemodynamic measurements (pulmonary artery pressures and cardiac output) were obtained at 2, 4, 8 and 12 hours (in some cases at 24 and 48 hours) and also whenever clinically indicated.

A twelve-lead ECG was obtained on arrival in the intensive care unit and during post-operative days 1, 2, 3 and at hospital discharge. Creatinine phosphokinase MB band (CK-MB) was obtained every 8 hours for 48 hours and when indicated. Radio-nuclide ventriculography for ejection fraction and wall motion score was done about 14 days post-operation and as close to hospital discharge as possible. Other tests and measurements (e.g., chest x-ray, pulmonary artery wedge pressure (PCWP) were performed when clinically indicated for diagnosis or evaluation of myocardial infarction, or congestive heart failure. Timing and dose of all cardiovascular medications within 48 hours after surgery were recorded. The total dose of all analgesics during the 24-hour post-operative period was recorded. Fluid intake and output (e.g., blood replacement and urine output) were recorded for 48 hours. The type and duration of inotropic support and antiarrhythmic intervention required were recorded through 24 hours after surgery. Two-channel Holter recordings were obtained during 3 periods, the eight hours prior to intubation, from intubation through the end of surgery, and for an additional 24–48 hours after surgery.

Safety Assessment

In addition to the hemodynamic monitoring described above the following tests were performed at screening, on the first post-operative day and at discharge:

1. Hematology included hemoglobin, total white cell count and differential, hematocrit and platelet count.
2. Biochemistry included serum sodium, potassium, chloride, phosphorus, magnesium, urea, creatinine, serum glutamic pyruvic transaminase (SGPT), serum glutamic oxaloacetic transaminase (SGOT), total bilirubin, albumin, total protein, uric acid, alkaline phosphatase, creatine phosphokinase and CPK-MB. CPK-MB was also measured every 8 hours for the 48 hours following chest closure. Blood glucose and uric acid levels were measured before infusion, cardiopulmonary bypass (CPB), after CPB, upon arrival in the intensive care unit (ICU) and at 4 and 8 hours thereafter. The levels were also measured 24 hours post CPB and at discharge.
3. Urinalysis included blood, pH, protein, glucose, ketones, red blood cell, white blood cell casts and crystals. Urine was also collected before treatment, at the end of infusion, and 4 to 8 hours after the end of infusion, for determination of uric acid content.
4. Any adverse events were recorded throughout by the investigator, who assessed their severity and the relationship of these adverse experiences to the treatment.

Efficacy Assessment

One measure of efficacy was the degree to which AICA riboside lowered the incidence, duration and/or severity of ischemic events (by comparison of S-T segment changes on continuous Holter recordings before, during and for 48 hours after the procedure). The efficacy of AICA riboside in reducing the deleterious effects of ischemia on myocardial mechanics (by assessment of regional wall motion on TEE during the pre- and post-bypass periods, and by measurement of ejection fraction pre- and post-operatively), was also determined. The evaluation of Holter tapes and echo videotapes was performed centrally by two independent blinded observers; if there was disagreement between the two, a third observer was used to "break the tie." The same observers were used throughout the study.

The incidence of adverse clinical outcomes, such as cardiac death (death of patient attributable to primarily cardiac causes, non-fatal transmural MI (as measured by the appearance of a new Q-wave on 12-lead ECG plus a CK-MB value of $\geq 50$ units), non-transmural MI (CK-MB value of $\geq 50$ units), congestive heart failure (low cardiac output requiring intra-aortic balloon pump or left ventricular assist device) or life-threatening dysrhythmia (ventricular fibrillation, or ventricular tachycardia requiring cardioversion or drug treatment) was compared between the placebo and treatment groups. For the diagnosis of myocardial infarction, ECG tracings and CK-MB values were assessed centrally by observers blinded to treatment. The difficulty of weaning the patient from bypass, if any, was compared between placebo and treatment groups by noting need for one or more of the following: pacemaker, return to bypass, balloon pump or use of vasopressors.

Statistical Analysis

The results reported herein do not cover all the parameters measured but address the measurements listed below using the methods indicated.

1. Group Comparability. To assess the comparability among the three treatment groups, the following baseline and intra-operative measurements were evaluated using one-way analysis of variance for continuous variables and chi-square tests on contingency tables for discrete variables.

2. Baseline. Age, sex, cardiovascular history (angina, hypertension, prior MI, CHF, arrhythmia), ejection fraction, catheterization data (number of stenosed vessels), number of pre-bypass ischemic events and minutes per hour of ischemia (measured by Holter ECG).

3. Intra-operative. Number of grafted vessels, aortic cross-clamp time, surgery time, bypass time.

4. Clinical Outcome. Outcomes of cardiac death, MI, CHF and life-threatening dysrhythmia were compared. Specific endpoints for analysis were combined into a dichotomous endpoint, i.e., at least one of the four events listed above occurs versus none occurs. Fisher's exact test for small samples was used to compare the rates of clinical outcome between the three treatment groups. The same comparison was done of the combined active treatments vs. placebo.

5. Ischemic Events—TEE. Ischemic event data were evaluated during two time periods—pre-bypass and post-bypass, using the following analysis:
   a) The number of patients with ischemic events was compared across the groups using Fisher's exact test. This analysis also included pre-post changes and pre- and post-combined.
   b) For patients with events, analysis of the mean duration and severity of ischemia was done. Using only the patients with ischemic events reduced the number included in the analysis, but allowed determination of whether the drug is effective in reducing the magnitude of the events, should they occur. The distribution for duration of ischemia was found to be skewed, so a $\log_{10}$ transformation was used to induce a normal distribution and one-way ANOVA was used to compare the groups. For severity (an ordinary variable, 0–4 scale) and number of events, the Kruskal-Wallis nonparametric test was used. The same comparisons were done with the active treatment groups combined.

6. Ischemic Events—ECG. The analysis of ischemic events indicated by ECG was done using the same methods as the echo events. The time periods analyzed were: (a) baseline (Holter start to infusion start), (b) pre-bypass (infusion start to bypass start), (c) post-bypass (sideclamp off to infusion end), and (d) post-treatment (infusion end to Holter end). For patients with events, the following variables were analyzed: mean duration, maximum ST change and area under the curve of significant ST segment deviation. Analysis of variance (ANOVA) was used. The same comparisons were done with the active treatment groups combined.

7. Ischemia vs. Outcome. The relationships between ischemia (TEE and ECG) detected during the time periods outlined above, and clinical outcomes were analyzed using Fisher's exact test (See J. Leung, et al.: Prognostic Importance of Postbypass Regional Wall-Motion Abnormalities in Patients Undergoing Coronary Artery Bypass Graft Surgery. *Anesthesiology* 71:16–25, 1989).

8. Difficulty in Weaning. Patients were considered to have difficulty in weaning if they needed one or more of the following interventions: pacemaker, return to bypass, balloon pump or use of vasopressors. The number of patients receiving each of the above interventions was analyzed using a $X^2$ and Fisher's exact test, as was the number of patients classified as having difficulty in weaning. In addition, the time to weaning (defined as time from cross-clamp removal to end of bypass) in the patients experiencing difficulty were compared by a 1-way analysis of variance.

9. Election Fraction. Pre-operative and post-operative ejection fractions were measured using different methodologies; therefore, changes could not be analyzed statistically. Group mean injection fractions and pre- and post-CABG are presented and apparent differences between groups were described.

10. Plasma Levels. AICA riboside plasma levels were measured to check agreement with randomized treatment and to document dose-proportionality and to assess plasma levels achieved. Individual values and group means were tabulated and drug clearance calculated. Dose proportionality was assessed.

11. Adverse Effects. The incidence, severity and drug-relatedness of any adverse effects were tabulated by treatment group by decreasing incidence of such effects in the high dose group. Statistical analysis was not performed.

12. Laboratory Data. For selected parameters of interest, individual values, mean changes and percent changes from baseline were tabulated and plotted over time by treatment group. The following parameters were addressed:

Urine—uric acid, creatinine, uric acid/creatinine ratio, pH, volume, crystals. All values were tabulated as mean ± S.E.M.

Blood Chemistry—CPK, CK-MB, uric acid, glucose. All values were tabulated as mean ± S.E.M.

Results

The studies described herein represent the first exposure of prolonged continuous infusion of AICA riboside to patients undergoing anesthesia, heart-lung bypass surgery and hypothermia. Dose levels had been evaluated using results from healthy volunteer subjects or conscious normothermic patients, and there was uncertainty as to the applicability of pharmakinetic studies using short infusion periods in healthy volunteer subjects or conscious normothermic patients.

The first six patients included in the study were given doses of 0.19 mg/kg/min and 0.38 mg/kg/min. When plasma levels of AICA riboside were measured, they were unexpectedly found to be approximately 2–4 times higher than anticipated. While applicant does not wish to be bound by any particular theory, higher AICA riboside levels may have resulted because of reduced drug metabolism due to low liver blood flow and hypothermia. The higher levels may also have been due to the effect of prolonged infusions on clearance rate. The dose levels were reduced from 0.19 and 0.38 mg/kg/min to 0.05 and 0.1 mg/kg/min. This then achieved the steady state plasma concentrations of approximately 2.5 and 5.0 µg/ml in subsequent patients.

Results from these first 6 patients, who were studied at the initial high dose, are summarized below and were included in the overall safety analysis. Except for patient A4 who received placebo, these results were not included in evaluation of efficiency unless expressly stated with respect to such results.

In the initial high dose group there were four patients who received the lower dose (0.19 mg/kg/min), one who received the high dose (0.38 mg/kg/min) and one placebo patient. In general, the drug was well tolerated and there were no serious adverse experiences. As shown in Table 1, blood glucose levels were elevated in all patients at most times; there were no values below the limits of normal. There was significant hyperuricemia and elevated urinary uric acid levels with crystalluria, which necessitated irrigation of the urethral catheter in the five drug-treated patients (Table 1). In these patients, the urine had a clear, green coloration, presumed to be due to high concentrations of AICA riboside and/or its breakdown products. Also, as shown by the data in Table 1, blood glucose levels were not decreased.

Apart from these effects on plasma and urine uric acid levels and crystalluria, there were no adverse events considered to be related to treatment with AICA riboside. At the lower dose (0.19 mg/kg/min), 2 of the 4 patients (A3 and A6) had no adverse events, 1 patient (A1) had extrasystoles, labile blood pressure and an episode of low blood $PO_2$, which were corrected uneventfully. This patient also had a recto-sigmoid carcinoma, clearly not related to drug treatment and for which appropriate therapy was instituted. The fourth low dose patient (A2) had an episode of complete heart block post-bypass, followed by hypertension some 4 hours later. Patient A5, who received 0.38 mg/kg/min, had no events other than S-T segment elevation on the ECG post-bypass.

Patient Characteristics

Tables 2 and 3 show clinical and surgical data considered to be of prognostic importance for perioperative morbidity. No significant differences were found in any of the parameters, with the following exceptions: all patients in the placebo and high dose group, but only 83% of the low dose group, had a history of stable angina (p=0.021); there were 3 females in the low dose group, none on the high dose and 1 in the placebo group (p=0.090). It was concluded that overall the groups were well matched in respect of demographics, severity of illness and extent of surgical procedure.

TABLE 2

PREOPERATIVE CLINICAL DATA

| Variable | 0.05 mg/kg/min | 0.1 mg/kg/min | Placebo |
|---|---|---|---|
| | Number of Patients | | |
| | 41 | 35 | 37 |
| Age in years | 60.4 ± 1.6 | 62.7 ± 1.5 | 63.8 ± 1.5 |
| Males (%) | 34 (83) | 33 (94) | 34 (92) |
| Females (%) | 7 (17) | 2 (6) | 3 (8) |
| Baseline Ischemia by Holter (%) | 3 (15) | 5 (14) | 3 (8) |
| Stable Angina (%) | 33 (80) | 35 (86) | 34 (92) |
| Unstable Angina (%) | 18 (44) | 14 (40) | 15 (41) |
| Valvular Disease (%) | 2 (5) | 0 (0) | 0 (0) |

TABLE 1

LABORATORY DATA - SERUM GLUCOSE AND URIC ACID LISTING BY PATIENT (in mg/dl)
FIRST SIX PATIENTS ONLY

| PATIENT | AICA RIBOSIDE TREATMENT GROUP | LAB TEST (NORMAL RANGE) | SCREENING | PRE INF | PRE CPB | POST CPB | ICU +0 HR | ICU +4 HR | ICU +8 HR | 24 HR POST | DISCHARGE |
|---|---|---|---|---|---|---|---|---|---|---|---|
| A-01 | 0.19 mg\kg\min | GLUCOSE (65–115 mg/dl) URIC ACID (3.5–8.5 mg/dl) | 80 5.6 | 89 6.2 | 91 7.7 | 254 (H) 9.5 (H) | 140 (H) 10.7 (H) | 171 (H) 9.2 (H) | 117 (H 8.8 (H) | 103 7.7 | 153 (H) 10.7 (H) |
| A-02 | 0.19 mg\kg\min | GLUCOSE (65–115 mg/dl) URIC ACID (3.5–8.5 mg/dl) | 138 (H) 5.8 | 162 (H) 5.1 | 147 (H) 6.9 | 302 (H) 8.5 | 213 (H) 10.7 (H) | 205 (H) 9.8 (H) | 190 (H) 9.2 (H) | 150 (H) 6.4 | 159 (H) 4.8 |
| A-03 | 0.19 mg\kg\min | GLUCOSE (65–115 mg/dl) URIC ACID (3.5–805 mg/dl) | 113 7.2 | 113 7.2 | 91 9.0 (H) | 222 (H) 9.8 (H) | 123 (H) 10.7 (H) | 152 (H) 9.2 (H) | 179 (H) 7.3 | 105 5.5 | 129 (H) 6.7 |
| A-04 | PLACEBO | GLUCOSE (65–115 mg/dl) URIC ACID (3.5–8.5 mg/dl) | 116 (H) 4.3 | 116 (H) 4.3 | 99 4.2 | 260 (H) 3.6 | 135 (H) 3.5 | 115 3.8 | 103 3.8 | 130 (H) 3.9 | 107 4.4 |
| A-05 | 0.38 mg\kg\min | GLUCOSE (65–115 mg/dl) URIC ACID (3.5–8.5 mg/dl) | 124 (H) 7.4 | 111 7.4 | 103 10.7 (H) | 227 (H) 13.5 (H) | 104 18.3 (H) | 144 (H) 16.4 (H) | 143 (H) 15.5 (H) | 137 (H) 12.6 (H) | 108 10.3 (H) |
| A-06 | 0.19 mg\kg\min | GLUCOSE (65–115 mg/dl) URIC ACID (3.5–8.5 mg/dl) | 104 5.7 | 104 5.7 | 97 6.8 | 222 (H) 6.9 | 104 10.0 (H) | 105 8.7 (H) | 103 7.8 | 99 6.0 | 109 8.6 (H) |

PRE INF = pre-infusion with AICA riboside or placebo
PRE CPB = pre-cardiopulmonary bypass
POST CPB = post-cardiopulmonary bypass
ICU +0 = upon arrival at intensive care unit
ICU +4 = four hours after arrival at intensive care unit
ICU +8 = eight hours after arrival at intensive care unit
24 HR POST = 24 hours after cardiopulmonary bypass
(H) Indicates a higher than normal range TABLE 2-continued

PREOPERATIVE CLINICAL DATA

| Variable | 0.05 mg/kg/min | 0.1 mg/kg/min | Placebo |
|---|---|---|---|
| | Number of Patients | | |
| | 41 | 35 | 37 |
| Hypertension (%) | 20 (49) | 19 (54) | 25 (68) |
| Hypercholesterolemia (%) | 18 (45) | 13 (37) | 18 (49) |
| Myocardial Infarction (%) | 17 (41) | 18 (51) | 17 (46) |
| Congestive Heart Failure (%) | 1 (2) | 0 (0) | 0 (0) |
| Cardiac Arrhythmia (%) | 7 (17) | 4 (11) | 4 (11) |
| Carotid Bruit (%) | 6 (15) | 8 (23) | 3 (8) |
| Ejection Fraction (%) | 55.0 ± 2.3 | 58.4 ± 2.4 | 57.6 ± 2.0 |
| LV End Diastolic Pressure-mm Hg | 15.3 ± 1.6 | 15.3 ± 1.7 | 12.8 ± 1.5 |
| Number of Stenosed Vessels | 3.3 ± 0.3 | 3.2 ± 0.2 | 3.9 ± 0.3 |

No differences approach statistical significance.

TABLE 3

SURGICAL DATA

| Variable | 0.05 mg/kg/min | 0.1 mg/kg/min | Placebo |
|---|---|---|---|
| | Patients (n) | | |
| | 41 | 34 | 36 |
| Crossclamp Time (mins) | 54.5 ± 2.5 | 52.4 ± 2.5 | 53.8 ± 2.9 |
| Bypass Time (mins) | 106 ± 4.9 | 99 ± 4.7 | 111 ± 6.7 |
| Surgery Time (mins) | 225 ± 9.3 | 215 ± 7.1 | 235 ± 8.8 |
| Number of Vessels Grafted | 3.2 ± 0.14 | 2.8 ± 0.14 | 3.2 ± 0.16 |

No differences were statistically significant.

Overall Evaluation

Adverse Events

In the setting of CABG surgery, adverse effects are expected to occur frequently. In this study, 29 of 37 placebo patients had one or more adverse events. The numbers of drug-treated patients with events were 30/35 in the high dose group (0.1 mg/kg/min), and 28/41 in the low dose group (0.05 mg/kg/min). There was no evidence that any of these events occurred more frequently in drug-treated patients compared with placebo.

Almost all of these events in all treatment groups were mild or moderate in severity and required no other specific medications. Five other events were categorized as severe; two acute myocardial infarctions (patients A26 and A39), one of whom also had CHF requiring intra-aortic balloon pump assistance, one pulmonary embolus (patient A12), and an arterial embolus to the right leg necessitating amputation (patient A14).

There has been 1 death in the study to date; patient A36, a 67-year-old male in the placebo group, had pre-operative unstable angina, poorly controlled hypertension and high grade left main disease. After an uncomplicated operative course, he developed respiratory distress in the intensive care unit and the ventilator was noted to be malfunctioning. External pacing and eventually internal cardiac massage, along with other resuscitation measures, were unsuccessful.

In virtually all cases (including all the severe events listed above), the events were considered by the investigators to be unrelated to drug, or that the probability that they were due to drug was remote, with the following exceptions: patient A2, who received 0.19 mg/kg/min, developed hyperuricemia and orange granules in urine, and patient A14, at the 0.05 mg/kg/min dose, whose urine developed the same green coloration already described in the initial high dose patients.

Serum Uric Acid and Glucose Levels

After the first six patients, the doses of AICA riboside were reduced, and there were no further clinical elevations in serum uric acid. As shown in Table 4a, mean changes showed a clear trend towards a dose-related increase in serum uric acid in the treated groups. However, clinically relevant hyperuricemia or crystalluria was not seen. During the procedure, infusion containing glucose was given. As shown in Table 4b, plasma glucose levels were elevated in all groups.

TABLE 4a

SERUM URIC ACID-MEAN CHANGES FROM BASELINE (in mg/dl)

| SAMPLE TIME | 0.05 mg\kg\min (n = 41) | 0.10 mg\kg\min (n = 35) | PLACEBO (n = 37) |
|---|---|---|---|
| MEAN BASELINE | 5.9 +/− 0.2 | 5.7 +/− 0.2 | 5.9 +/− 0.3 |
| PRE CPB | −0.1 +/− 0.1 | 0.4 +/− 0.1 | 0.6 +/− 0.1 |
| POST CPB | −0.6 +/− 0.1 | 0.4 +/− 0.1 | −1.6 +/− 0.1 |
| ICU + 0 | −0.3 +/− 0.1 | 1.5 +/− 0.2 | −1.7 +/− 0.1 |
| ICU + 4 HR | −0.1 +/− 0.1 | 1.6 +/− 0.2 | −1.2 +/− 0.3 |
| ICU + 8 HR | −0.0 +/− 0.1 | 1.4 +/− 0.2 | 1.3 +/− 0.1 |
| 24 HR POST | −0.5 +/− 0.2 | 0.3 +/− 0.3 | −1.2 +/− 0.2 |
| DISCHARGE | 0.3 +/− 0.2 | −0.1 +/− 0.2 | −0.2 +/− 0.3 |

TABLE 4b

SERUM GLUCOSE-MEAN CHANGES FROM BASELINE (in mg/dl)

| SAMPLE TIME | 0.05 mg\kg\min (n = 41) | 0.10 mg\kg\min (n = 35) | PLACEBO (n = 37) |
|---|---|---|---|
| MEAN BASELINE | 108.5 + 4.8 | 120.6 + 7.3 | 121.0 + 15.5 |
| PRE CPB | 18.6 + 7.0 | 4.8 + 3.4 | 14.5 + 4.4 |
| POST CPB | 116.5 + 10.7 | 120.6 + 15.9 | 138.0 + 14.7 |
| ICU + 0 | 65.6 + 7.6 | 59.8 + 13.6 | 96.3 + 12.8 |
| ICU + 4 HR | 53.6 + 11.9 | 55.5 + 9.6 | 76.5 + 14.6 |
| ICU + 8 HR | 58.8 + 12.1 | 44.4 + 7.5 | 65.6 + 12.4 |
| 24 HR POST | 44.2 + 7.4 | 27.2 + 7.3 | 45.0 + 6.3 |
| DISCHARGE | 18.7 + 6.3 | 19.2 + 7.0 | 18.6 + 9.0 |

(See Table 1 for explanation of abbreviations)

Clinical Efficacy

1. Transmural Myocardial Infarction. Transmural myocardial infarction, defined as the appearance of a new Q-wave on post-operative 12-lead ECG and CK-MB level ≧50 I.U., occurred in 5 patients in the placebo group, in 2 of the patients receiving low dose AICA riboside, and in 2 of the high dose patient (Table 5). Differences between the groups were not statistically significant by Fisher's exact test, nor was significance achieved when the two treatment groups combined were compared with placebo (p=0.15). However, in view of the small number of subjects per group, these results (64% reduction in the frequency of post-operative myocardial infarctions) show a trend toward a decrease in transmural MI with AICA riboside treatment.

TABLE 5

NUMBER OF PATIENTS IN EACH TREATMENT GROUP DEVELOPING TRANSMURAL MYOCARDIAL INFARCTION (NEW Q-WAVE ON POST-OPERATIVE 12-LEAD ECG AND CK-MB ≧ 50 I.U.)

|  | 0.05 mg/kg/min | 0.10 mg/kg/min | Placebo |  |
| --- | --- | --- | --- | --- |
|  | Number of Patients | | | |
|  | 41 | 35 | 37 | |
| Myocardial Infarction | 2 (4.9%) | 2 (5.7%) | 5 (13.5%) | p = 0.42 |

All of the infarctions were present either on arrival in the intensive care unit or on post-operative day 1. One of the patients who developed myocardial infarction (A39) also required an intra-aortic balloon pump for severe hypotension on weaning from the pump; with this exception, none of the other outcomes being evaluated (CHF requiring intra-aortic balloon pump or left ventricular assist device, cardiac death or life-threatening arrhythmia) occurred in any of the three groups.

2. Non-Transmural Myocardial Infarction. Clinically significant elevation of creatinine phosphokinase MB band (CK-MB) levels, ≧50 I.U., with or without S-T segment elevation, with or without appearance of new Q-waves on 12-lead ECG, was observed in 17 (47%) placebo patients, 13 (13.7%) patients receiving low dose AICA riboside, and 8 (23.5%) in the high dose group (p=0.10, $X^2$ test) (Table 6). For the combined treatment groups versus placebo, the result was statistically significant (p=0.046).

TABLE 6

NUMBER OF PATIENTS IN EACH TREATMENT GROUP WITH NON-TRANSMURAL MYOCARDIAL INFARCTION (CK-MB ≧ 50 I.U.)

|  | 0.05 mg/kg/min | 0.01 mg/kg/min | Placebo |
| --- | --- | --- | --- |
|  | No. of Patients | | |
|  | 41 | 35 | 37 |
| CK-MB ≧ 50 | 13 (13.7%) | 8 (23.5%) | 17 (47%) |

Across all patients, there was a trend toward a reduction in total CK levels in the treated groups compared with placebo (Table 7a). This same trend was apparent in CK-MB release (Table 7b).

TABLE 7a

CK-MB-MEAN CHANGES FROM BASELINE (in U/L)

| SAMPLE TIME | 0.05 mg/kg/min (n = 41) | 0.10 mg/kg/min (n = 35) | PLACEBO (n = 37) |
| --- | --- | --- | --- |
| MEAN BASELINE | 0.2 +/− 0.1 | 0.1 +/− 0.1 | 0.2 +/− 0.1 |
| ICU + 0 | 24.5 +/− 2.7 | 25.2 +/− 2.3 | 33.3 +/− 7.4 |
| ICU + 8 HR | 37.1 +/− 5.1 | 34.3 +/− 6.2 | 44.6 +/− 7.3 |
| ICU + 16 HR | 30.8 +/− 4.9 | 25.9 +/− 6.7 | 44.7 +/− 10.0 |
| ICU + 32 HR | 9.2 +/− 2.5 | 12.8 +/− 4.5 | 20.2 +/− 6.4 |
| ICU + 40 HR | 7.7 +/− 2.2 | 7.1 +/− 3.0 | 11.7 +/− 2.9 |
| ICU + 48 HR | 3.9 +/− 1.5 | 3.5 +/− 2.1 | 3.9 +/− 1.7 |
| 24 HR POST | 23.5 +/− 5.0 | 21.1 +/− 5.3 | 39.7 +/− 11.3 |
| DISCHARGE- | 0.0 +/− 0.1 | 0.4 +/− 0.4 | 0.7 +/− 0.4 |

TABLE 7b

CK-MEAN CHANGES FROM BASELINE (in U/L)

| SAMPLE TIME | 0.05 mg/kg/min (n = 41) | 0.10 mg/kg/min (n = 35) | PLACEBO (n = 37) |
| --- | --- | --- | --- |
| MEAN BASELINE | 89.2 +/− 30.9 | 66.6 +/− 11.3 | 118.2 +/− 51.7 |
| ICU + 0 | 346.2 +/− 45.3 | 386.1 +/− 51.8 | 323.3 +/− 46.8 |
| ICU + 8 HR | 839.2 +/− 89.3 | 869.6 +/− 143.7 | 965.6 +/− 140.3 |
| ICU + 16 HR | 1040.6 +/− 120.3 | 891.0 +/− 148.3 | 1136.4 +/− 136.2 |
| ICU + 32 HR | 874.7 +/− 126.3 | 894.0 +/− 142.9 | 1002.9 +/− 143.9 |
| ICU + 40 HR | 806.6 +/− 145.6 | 641.7 +/− 119.7 | 794.0 +/− 110.0 |
| ICU + 48 HR | 784.0 +/− 149.9 | 499.8 +/− 100.5 | 876.7 +/− 202.4 |
| 24 HR POST | 1028.1 +/− 126.4 | 1025.4 +/− 146.8 | 1226.7 +/− 161.8 |
| DISCHARGE | 87.8 +/− 46.6 | 31.9 +/− 22.0 | 34.1 +/− 69.0 |

3. Myocardial Ischemia. Myocardial ischemia was measured with continuous Holter ECG and TEE. Continuous Holter ECG was performed from the day before surgery through postoperative day No. 2. ECG episodes of ischemia were defined as reversible S-T depression 1 mm or greater lasting 1 minute or longer. TEE data were recorded continuously during surgery at the level of the mid-papillary muscles of the left ventricle. The wall motion of each of the four segments was graded from 0–4 (normal to dyskinesis). TEE ischemia was defined by regional wall motion worsening at least 2 grades and lasting 1 minute or longer. There was no difference in the incidence (percent of patients with ischemia) or severity of preoperative (baseline) ECG ischemia in the placebo, low dose and high dose groups (18%, 14% and 14% ischemia, respectively). In the prebypass period, the incidence of ECG ischemia was similar in the placebo, low dose and high dose groups (0%, 3% and 3%, respectively). The incidence of TEE ischemia tended to be lower in the high dose group (6%) versus placebo (19%) and low dose (15%), p=0.22. In the postbypass period, the incidence of TEE ischemia was similar in the placebo, low dose and high dose groups (29%, 27% and 24% ischemia, respectively); p=0.86.

The incidence of ECG ischemia tended to be lower in the high dose group (11%), than in the placebo or low dose groups (18% and 22%, respectively), p=0.42. As shown in Table 8, in those patients who experienced ischemia events, the severity of postbypass ECG ischemic episodes was less severe in the high dose group than in the low dose or placebo groups, judged by mean duration, mean area under the S-T curve (AUC), in millimeter minutes (mm-min), and ischemic minutes per hour (Isch min/h) monitored.

TABLE 8

|  | Placebo | Low Dose | High Dose | p-Value |
| --- | --- | --- | --- | --- |
| Mean Duration (min) | 175 ± 156 | 125 ± 80 | 36 ± 20 | 0.04 |
| Mean AUC (mm-min) | −258 ± 317 | −172 ± 144 | −52 ± 28 | 0.24 |
| Isch min/h monitored | 35 ± 14 | 40 ± 15 | 27 ± 20 | 0.22 |

These data indicate that AICA riboside limits the extent of postsurgical myocardial ischemia in patients undergoing CABG surgery.

Difficulty in Weaning from Bypass

As noted, patients were determined as being difficult to remove from cardiopulmonary bypass if they required one or more of the following interventions: insertion of a pacemaker, return to bypass, use of a balloon pump or administration of vasopressors, or another intervention which the investigation determines is indicative of difficulty in weaning. There were no significant differences between the groups in respect to need for pacemaker, return to bypass or balloon pump assist. Both the low dose group and the high dose group showed a strong trend towards a reduced need for vasopressor support (p=0.19). See Table 9a. When a combination of the high and low dose groups were compared to placebo (Table 9b), the reduced need for vasopressor support approached statistical significance (p=0.08). As a result of the reduced need for vasopressor support in the high and low drug treated groups, combined with a slight reduction in the need for other support in these patients, there was a strong trend (p=0.17 when compared separately and p=0.06 when combined dose groups were compared with placebo) towards a reduction in weaning difficulty in the drug treated groups. There were no differences in any of the weaning difficulty parameters discussed above between the high and low dose groups (Table 9c).

With respect to weaning time as measured as the time from cross-clamp removal to termination of bypass, there were no statistically significant differences between the groups. If, however, only patients that had difficulty in weaning from bypass (as described above) were evaluated, there was a strong trend toward the reduction in the time seen in the drug treated patients (Table 9d).

TABLE 9a

WEANING DIFFICULTY, BY TYPE OF DIFFICULTY

| | 0.05 mg/kg/min | 0.10 mg/kg/min | Placebo | |
|---|---|---|---|---|
| | | Patients (n) | | |
| | 41 | 35 | 37 | p-value |
| Pacemaker | 4 (9.8%) | 4 (11.4%) | 2 (5.1%) | 0.7 |
| Return to Bypass | 0 | 0 | 1 (2.7%) | 0.6 |
| Vasopressors | 3 (7.3%) | 4 (11.4%) | 8 (21.6%) | 0.19 |
| Balloon Pump | 0 | 0 | 1 (2.7%) | 0.6 |
| Other | 3 (7.3%) | 4 (11.4%) | 5 (13.5%) | 0.7 |

TABLE 9b

VASOPRESSOR WEANING DIFFICULTY
(0.05 + 0.1 mg/kg/min VS PLACEBO)

| | 0.05 + 0.10 | Placebo | p-value |
|---|---|---|---|
| Vasopressors Required | 7 (9.2%) | 8 (21.6%) | 0.08 |

TABLE 9c

PATIENTS WITH ANY DIFFICULTY WEANING

| 0.05 | 0.10 | Placebo | |
|---|---|---|---|
| | Patients (n) | | |
| 41 | 35 | 37 | p-value |
| 7 (17%) | 8 (23%) | 13 (35%) | 0.17 |

| 0.05 + 0.10 | | Placebo | |
|---|---|---|---|
| | Patients (n) | | |
| 76 | | 37 | p-value |
| 15 (19.7%) | | 13 (35.1%) | 0.06 |

TABLE 9d

WEANING TIME

| | 0.05 mg/kg/min | 0.1 mg/kg/min | Placebo |
|---|---|---|---|
| | | Patients (n) | |
| Group | 41 | 34 | 36 |
| All Patients | 20 +/− 2.2 | 17 +/− 1.8 | 23 +/− 2.9 |
| Pts with Difficulty | 20 +/− 4.6 | 20.8 +/− 4.2 | 31.8 +/− 6.3 |
| Pts without Difficulty | 20.4 +/− 2.5 | 16.3 +/− 1.9 | 17.9 +/− 2.2 |

Hemodynamic Efficacy

Results for ejection fraction, measured on all patients pre-operatively (by angiography) and at the time of discharge from the intensive care unit (by radionuclide ventriculography) are given in Table 10 below.

TABLE 10

Ejection Fraction (%) Measured Before (by LV Angiography) and After (by Radionuclide Ventriculography) Surgery (p = 1-way ANOVA)

| Period | 0.05 mg/kg/min | 0.10 mg/kg/min | Placebo | |
|---|---|---|---|---|
| Pre-Bypass | 55.0 ± 2.3 | 58.4 ± 2.4 | 57.6 ± 2.0 | p = 0.54 |
| Post-Bypass | 59.0 ± 2.0 | 61.3 ± 1.7 | 56.5 ± 2.3 | p = 0.28 |

At baseline, the groups were reasonably similar in respect to ejection fraction. Post-operatively, although the difference was not statistically significant, the AICA riboside groups had higher mean ejection fractions post-bypass than the placebo group.

Pharmacokinetics

Figure 1A:
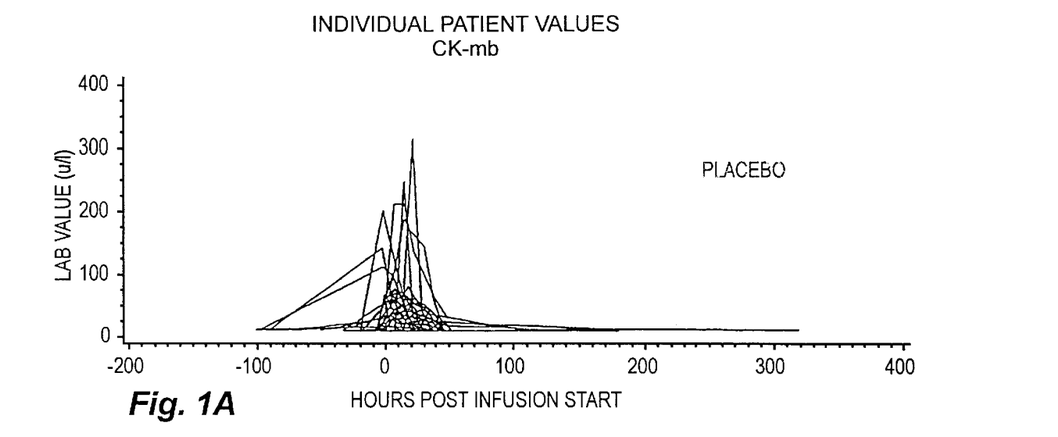
FIG. 1A is a graphical representation of individual patient values of creatinine phosphokinase MB band (CK-MB) levels in placebo patients (n=37) for patients in the study described in Example 1.
Figure 1B:
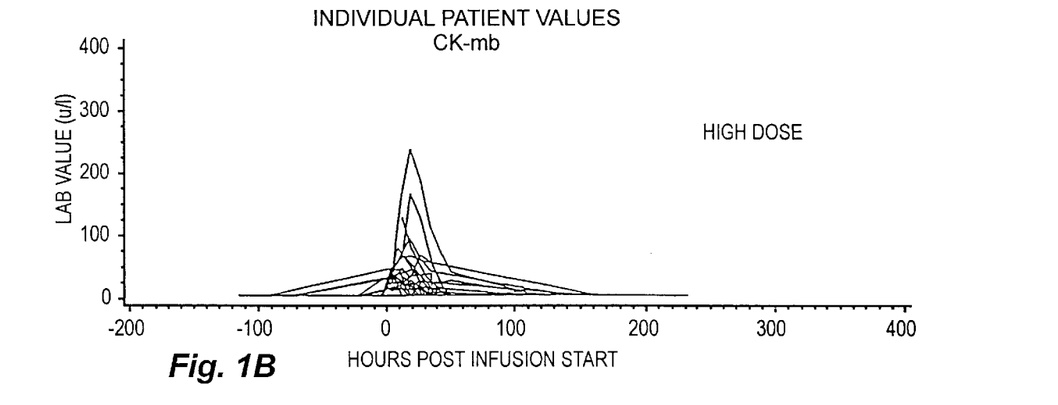
FIG. 1B is a graphical representation of individual patient values of creatinine phosphokinase MB band (CK-MB) levels in high dose (0.01 mh/kg/min.) AICA riboside (n=35) for patients in the study described in Example 1.
Figure 1C:
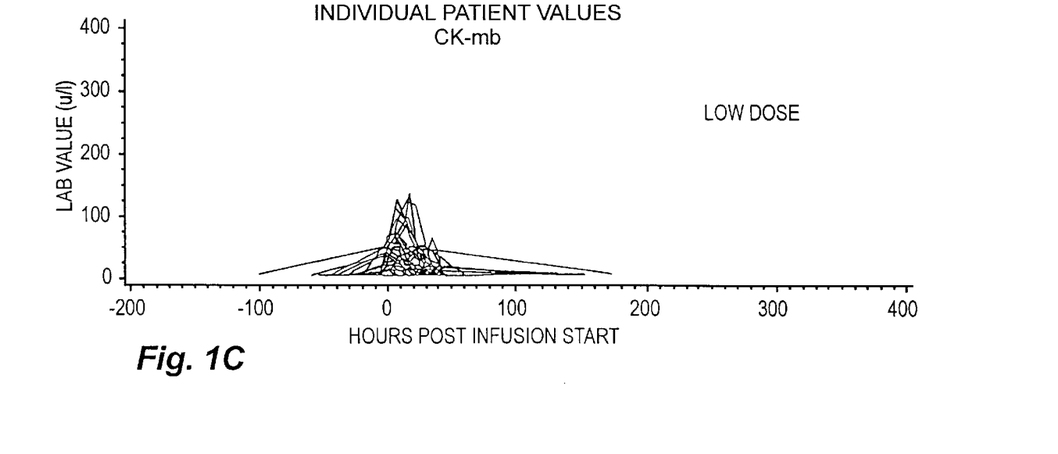
FIG. 1C is a graphical representation of individual patient values of creatinine phosphokinase MB band (CK-MB) levels in low dose (0.05 mg/kg/min.) AICA riboside (n=41) for patients in the study described in Example 1.
Figure 2:
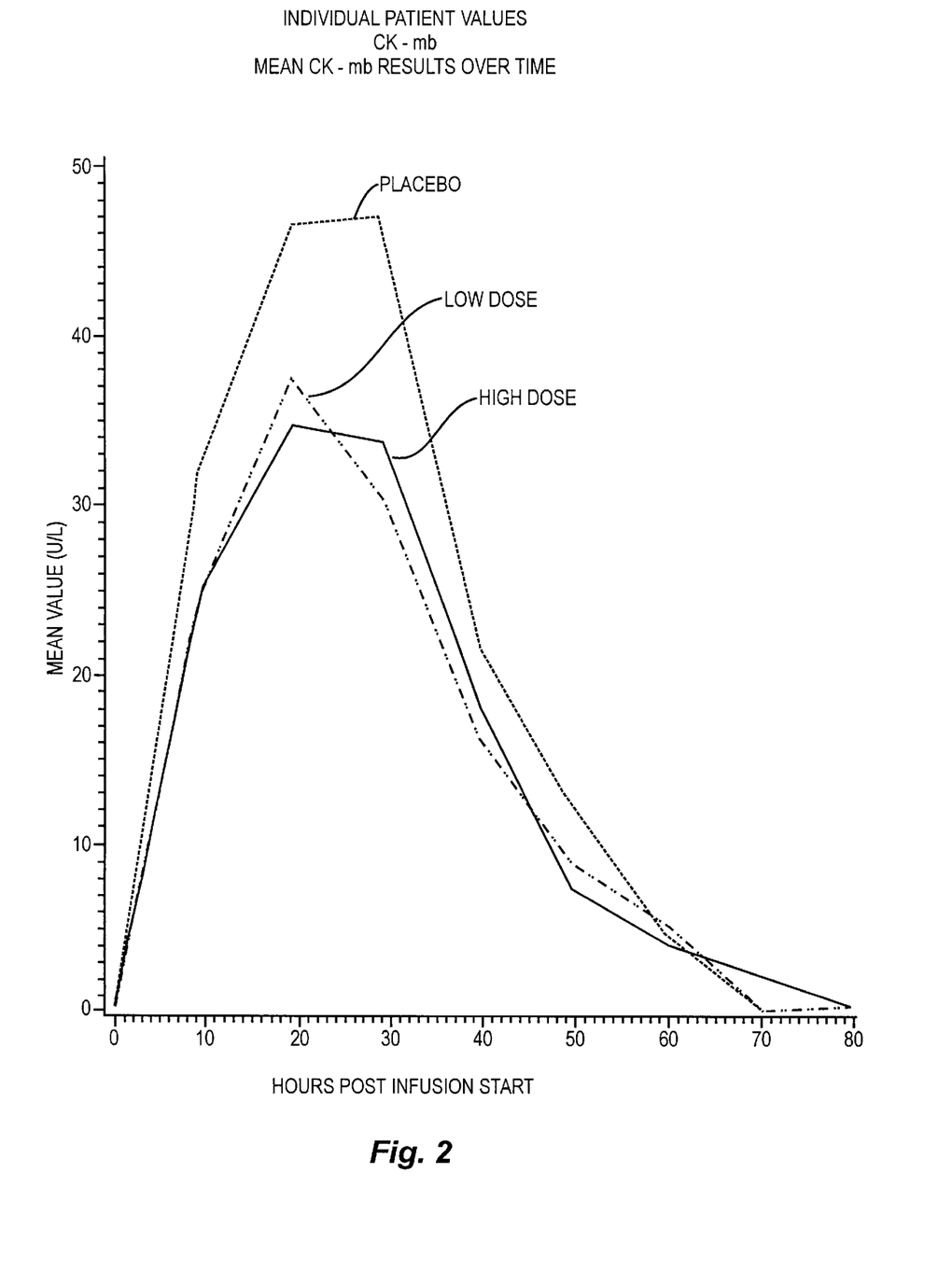
FIG. 2 is a graphical representation of mean creatinine phosphokinase MB band values for each treatment group over time, for the patients in the study described in Example 1.
Figure 3:
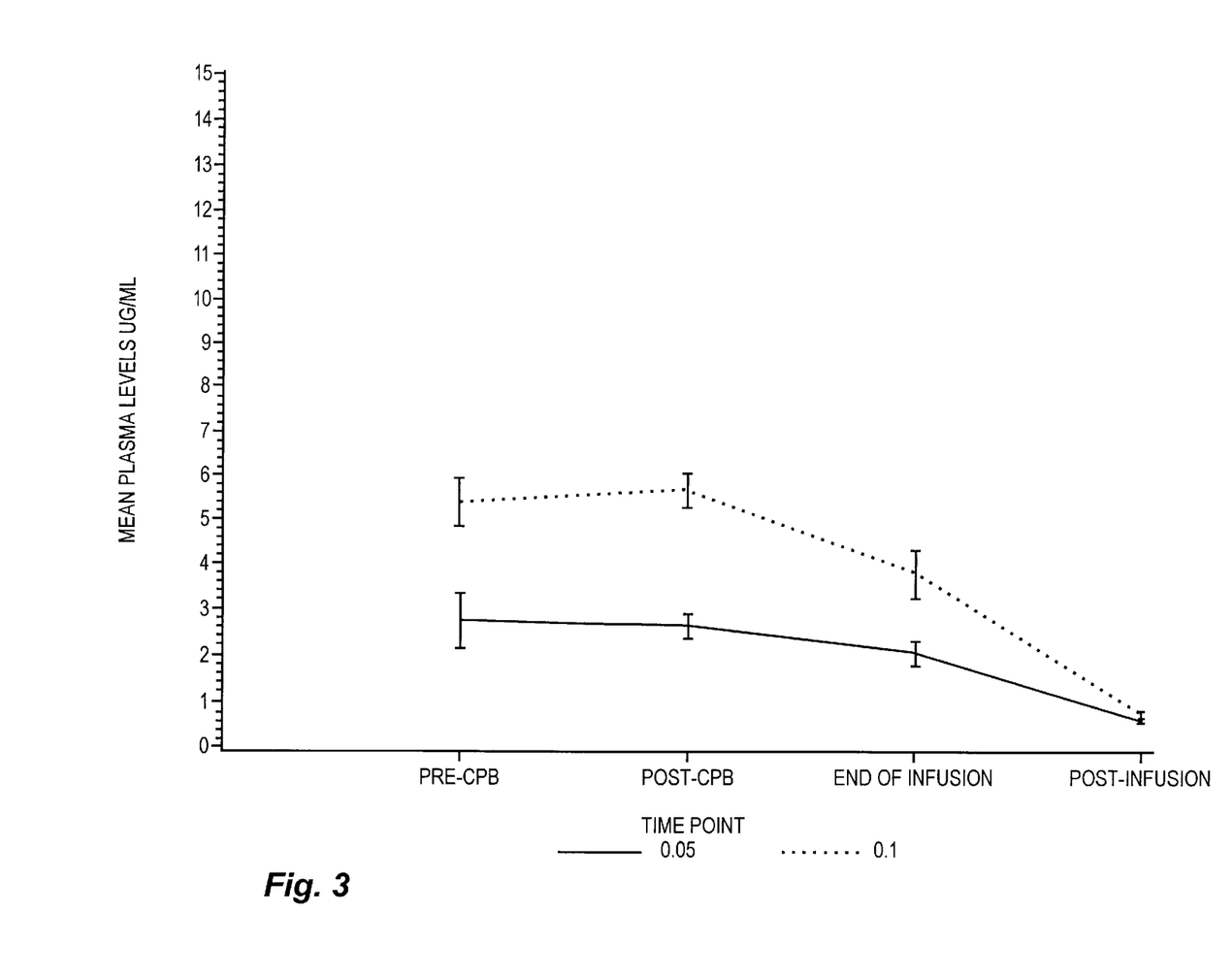
FIG. 3 is a graphical representation showing the mean plasma concentration of AICA riboside ($\mu$g/ml) during and following constant infusion of 0.05 or 0.1 mg/kg/min of the drug to patients during CABG surgery, for the patients in the study described in Example 1. The solid line shows 0.05 mg/kg/min and the dotted line shows 0.1 mg/kg/min.

Table 11 below gives the mean plasma AICA riboside concentrations at pre-bypass, post-bypass, end of infusion and 60 minutes post-infusion for 40 patients receiving 0.05 mg/kg/min and 31 patients at the dose of 0.1 mg/kg/min. The data are also presented graphically in FIG. 3.

TABLE 11

Mean (±SEM) plasma AICA riboside concentrations (μg/ml) during and following constant infusion of 0.05 (n = 40) or 0.10 mg/kg/min (n = 31) of AICA riboside to patients undergoing CABG surgery

| Sample Time | 0.05 mg/kg/min | 0.10 in/kg/min |
| --- | --- | --- |
| Pre-Bypass | 2.66 ± 0.30 | 5.11 ± 0.20 |
| Post-Bypass | 2.49 ± 0.13 | 5.47 ± 0.19 |
| End Infusion | 1.83 ± 0.13 | 3.67 ± 0.30 |
| 1 Hour Post-Infusion | 0.32 ± 0.63 | 0.45 ± 0.03 |

Desired steady state plasma concentrations of 2.5 and 5.0 μg/ml for the low and high dose, respectively, were closely approximated at the pre- and post-bypass times, indicating good dose proportionality. Mean estimates of total plasma clearance ($CL_p$) were about the same for the low and high doses at both these times, approximating 1.2 L/hr/kg (range 1.1 to 1.2 L/hr/kg). This indicates that AICA riboside exhibits linear kinetics in patients undergoing CABG surgery at the infusion rates used in this study. These clearance rates are approximately 40–50% of those previously seen in conscious, healthy male subjects. Dixon, R., et al., *J. Clin. Pharm.* 31:342–347 (1991). While applicant does not wish to be bound by any particular theory, this difference in drug clearance may be a consequence of reduced metabolism due to hypothermia, decreased tissue uptake, lowered liver blood flow during the CABG procedure, or changes in metabolism associated with prolonged infusion. During the post-bypass period, there was a trend for the $CL_p$ to increase, the change coinciding with increase in body temperature and liver blood flow and discontinuation of anesthesia at this time. Once the infusion was terminated, the plasma AICA riboside concentrations declined rapidly to 10% of steady state levels after one hour.

Discussion

Perioperative myocardial infarction (MI) is not an uncommon complication of CABG surgery, with reported incidence of 10 to 50 percent, depending on the criteria used for diagnosis. Recent studies report an adverse effect of perioperative MI on immediate mortality rate, long-term survival or both (See H. Schaff, et al., *J. Thorac. Cardiovasc. Surg.* 88:972–981 (1984); P. Val. et al., *J. Thorac. Cardiovasc. Surg.* 86:878–886 (1983); W. Fennell et al., *J. Thorac. Cardiovasc. Surg.* 78:244–253 (1979); R. Seitelberger, et al., *Circulation* 83:460–468 (1991).)

The present study shows that AICA riboside protects against the adverse effects of tissue ischemia, prevents irreversible myocardial cell necrosis, and reduces the extent of cardiac functional impairment resulting from ischemic damage when given throughout the perioperative period, including immediately post-surgery (post-operative reperfusion) and by admixture with cardioplegic solution.

The results of the experiments described herein indicate a trend towards a lower incidence of transmural MI, evaluated using both new Q-waves and serum enzyme changes, between placebo (13.5%) and the low and high doses of AICA riboside (4.9% and 5.7%, respectively). This trend is even more apparent in the reduction of non-transmural MI, i.e., CK-MB levels greater than 50 I.U. in the absence of ECG changes (placebo 47.2%, low dose 31.7%, high dose 23.5%).

Although a strong trend (p=0.10) towards reduction of perioperative MIs was seen when the three groups were compared, these results did not reach significance. However, when all patients treated with drug (including the first 5 which received higher doses) are compared to placebo, there is a statistically significant reduction (p<0.05) in the rate of perioperative infarction in the drug treated group.

Applicant has also shown that AICA riboside alters the duration and severity of ischemic events. The mean duration of post-bypass ischemia events in placebo patients was 175 minutes (±156 minutes). Treatment with AICA riboside resulted in a reduction to 125 minutes (±80 minutes) in the low dose group and a reduction to 36 minutes (±20 minutes) in the high dose group in the average duration of post-bypass ischemia events (p=0.04). In addition, the number of post-bypass ischemic minutes per hour was lower in the high dose group (27±20) than in the placebo (35±14) and low dose (40±15) groups.

The severity of post-bypass ischemia was also lessened by administration of the high dose of AICA riboside. The mean area under the S-T segment was 35±14 and 40±15 in placebo and low dose patients, respectively. But administration of the high dose resulted in a value of 27±20.

AICA riboside also appeared to have an effect on pre-bypass ischemia, at least on the incidence of TEE ischemia (6% for high dose vs. 19% for placebo and 15% for low dose).

The results of this study also demonstrated improvement in the ability to wean patients from bypass. Patients who received AICA riboside were less likely to receive vasopressor assistance in order to regain post-bypass function. In fact, a nearly statistically significant improvement was seen in the reduced use of vasopressors in the drug treated group. This suggests that the patients who receive the drug are less compromised than patients in the placebo group.

Hemodynamic changes are difficult to interpret in the setting of CABG surgery; heart rate and blood pressure are to a large extent controlled by a variety of pharmacologic agents and adjustment of circulating volume, and no effects of treatment with AICA riboside were seen on these parameters. There was, however a trend towards higher ejection fraction in the high dose AICA riboside group immediately before discharge from the intensive care unit, compared with the placebo and the low dose group. Such an improvement in functional cardiac performance would be consistent with the effects on the level of ischemia and the incidence of myocardial infarction.

All of these results show beneficial effects of the administration of AICA riboside, especially in a dosage of about 0.1 mg/kg/min. When combined with the hyperuricemia and crystalluria issues associated with the administration of AICA riboside at a dosage of 0.19 mg/kg/min, and especially at a dosage of 0.38 mg/kg/min, these results show that the particularly therapeutic dosage of AICA riboside is about 0.1 mg/kg/min.

Conclusion

Those of ordinary skill in the art reviewing the above example will recognize that the data indicate that administration of AICA riboside will be safe and effective in the dosages described in preventing tissue damage resulting from undesired decreased blood flow. When administered in the dosages described herein, undesired clinical hyperuricemia and/or crystalluria can be avoided while effectiveness is maintained.

EXAMPLE 2

EFFECTS OF AICA RIBOSIDE IN PATIENTS UNDERGOING CORONARY ARTERY BYPASS GRAFT (CABG) SURGERY: PHASE 3 CLINICAL TRIALS

Like the experiments described in Example 1, the following experiments were conducted to evaluate the effects of AICA riboside administered to patients undergoing CABG surgery, and to determine effective dosages and concentrations of AICA riboside. Applicant discovered concentrations and dosages at which AICA riboside is effective compared to placebo in preventing adverse clinical outcomes, such as adverse cardiovascular events, including myocardial infarction and cardiac death. Applicant also discovered that AICA riboside is effective compared to placebo in preventing adverse cerebrovascular events, such as cerebrovascular accidents. Applicant has also discovered concentrations and dosages of AICA riboside that are particularly effective to reduce the combined incidence of adverse cardiovascular and cerebrovascular events. These concentrations and dosages of AICA riboside are also believed to be effective in preventing or reducing the incidences of congestive heart failure and life threatening dysrhythmia.

The study described in this Example 2 is a multicenter, placebo control, double blind, study performed in approximately 600 patients at 20 centers in the United States. Patients received the same dosing regimen as was administered in the study described in Example 1: either placebo or one of two AICA riboside doses (0.05 or 0.1 mg/kg/min for 7 hours). In all cases, AICA riboside was also administered in a 5 $\mu$g/ml concentration in the cardioplegia solutions of patients who received AICA riboside treatment.

The study described in this Example 2 differs from the study described in Example 1 in patient selection criteria. The study described in Example 1 excluded patients thought to be surgically and medically at highest risk during CABG surgery, that is, repeat CABG patients, emergencies and those who had poor left ventricular function. In the studies described in this Example 2, all patients undergoing CABG procedures were considered suitable to enter the study except that patients with recent or evolving myocardial infarctions were excluded so that new myocardial infarctions could be diagnosed. In addition, in Example 2 a wider selection of cardioplegia solutions was allowed reflecting typical surgical patterns of use.

The following Table 12 depicts a statistical analysis of the incidence of myocardial infarction (as defined by ECG and CK-MB levels, i.e., transmural MI), cerebrovascular accident, cardiac death, congestive heart failure and life-threatening dysrhythmia. As in Example 1, the low dose of AICA riboside is 0.05 mg/kg/min and the high dose is 0.1 mg/kg/min.

TABLE 12

INCIDENCE OF CLINICAL OUTCOMES

|  | Placebo | Low Dose | High Dose | p-value (high dose v.placebo) |
|---|---|---|---|---|
| Myocardial Infarction | 10 (4.7%) n = 211 | 9 (4.4%) n = 205 | 3 (1.5%) n = 203 | <0.05 |
| Cerebrovascular Accident | 9 (4.2%) n = 212 | 2 (0.9%) n = 214 | 1 (0.5%) n = 207 | <0.05 |
| Cardiac Death | 3 (1.4%) n = 212 | 5 (2.3%) n = 214 | 0 (0%) n = 207 | NS* |
| Congestive Heart Failure | 8 (3.8%) n = 212 | 6 (2.8%) n = 214 | 6 (2.9%) n = 207 | NS |
| Life-Threatening Dysrhythmia | 4 (1.9%) n = 212 | 9 (4.2%) n = 214 | 3 (1.4%) n = 207 | NS |
| Combined Clinical Outcomes | 29 (13.7%) n = 212 | 23 (10.7%) n = 214 | 11 (5.3%) n = 207 | <0.05 |

*Not statistically significant.

The MI data shown in Table 12 reflect diagnosis by both ECG and CK-MB. That is, those patients who showed either ECG indication of MI or CK-MB indication of MI (but not both) are excluded. The presence of a new Q-wave (Minnesota Code 1) was used to diagnose MI in ECG testing. CK-MB diagnosis of MI was made if at least one of the following criteria was met:

1. Elevation of CK-MB concentration to $\geq$100 ng/ml at any time post surgery and with the preceding or following CK-MB sample $\geq$50% of this peak value;
2. Elevation of CK-MB concentration to $\geq$70 ng/ml at any time after 12 hours post surgery and with the preceding or following CK-MB sample $\geq$50% of this peak value; or
3. A new elevation of CK-MB release, more than 24 hours after surgery, to a peak of $\geq$12 ng/ml with another measurement of at least 10 ng/ml immediately preceding or following the peak. If CK-MB levels were previously elevated, the levels must have fallen to below 10 ng/ml before the onset of this second elevation.

Diagnosis of cerebrovascular accident (CVA) was determined by signs and/or symptoms of significant neurologic deficit which persisted for over 24 hours. CVAs were considered study endpoints if there were focal neurological lesions lasting over 24 hours. Patients with non-focal lesions were considered as endpoints only if a neurological consultant diagnosed a CVA or if a CT or MRI scan was reported consistent with a new cerebral infarct or hemorrhage.

Cardiac death is defined as death of the patient from a primary cardiac cause, for example, myocardial infarction, dysrhythmia or ventricle dysfunction. All deaths were reviewed by a group of 3 independent cardiologists who lacked knowledge of the treatment group.

Diagnosis of congestive heart failure (CHF) was made by either: 1) severe worsening of left ventricular functions requiring an intraaortic balloon pump or left ventricular assist device for CI<1.5 l/min/m$^2$; or (2) cariogenic shock with CI<1.5 l/min/m$^2$ and PCWP>20 cm for >1 hour.

Diagnosis of life threatening dysrhythmia was made by either: (1) ventricular dysrhythmia requiring cardioversion; or (2) dysrhythmia requiring insertion of a pacemaker required at hospital discharge.

The combined outcome results in Table 12 show the incidence of the following adverse cardiovascular events: combined MI, CVA, cardiac death, CHF and life-threatening dysrhythmia. There appears to be a trend toward decreased incidence of adverse events in patients treated with the low dose of AICA riboside, however, the low dose appears to show no statistically significant efficacy. Thus, the p-values shown in Table 12 reflect a comparison of high dose (0.1 mg/kg/min) versus placebo.

Table 12 shows a 61% reduction in the incidence of combined outcomes in the high dose group compared to the placebo group (5.3% compared with 13%), with a p-value of <0.05.

The data indicate a 68% decrease in incidence of MI in the high dose group compared to the placebo group (1.5% compared with 4.7%), with a p-value of <0.05, and an 88% decrease in incidence of cerebrovascular accident in the high dose group compared to the placebo group (0.5% compared with 4.2%) (p-value <0.05). The data also show a strong trend toward a decrease in cardiac death (0 compared with 1.4%) in the high dose group compared with the placebo group with non-significant p-value.

For the adverse outcomes actions of congestive heart failure and life-threatening dysrhythmia, there appears to be a trend toward decreased incidence in the high dose group compared to the placebo group (CHF: 2.9% compared with 3.8%; dysrhythmia: 1.4% compared with 1.9%).

The incidence of all deaths tended to be lower in the high dose group than the placebo group (0.5% in the high dose group compared with 3.3% in the placebo group). The incidence of myocardial infarction as determined by either ECG or CK-MB tended to be lower in the high dose group compared to the placebo group (20.8% in the high dose group compared with 24.1% in the placebo group).

The uric acid concentrations of all patients in the study were monitored. While there is a clear dose related increase in uric acid concentrations in the treated patients, the plasma uric acid concentrations generally remained in, or close to, the normal range and there was no clinically significant crystalluria (data not shown).

Table 13 below depicts the incidence of myocardial infarction and combined clinical outcome (MI, CVA, cardiac death, CHF and life-threatening dysrhythmia) according to plasma level of AICA riboside. It is apparent from these data that the most effective plasma level of AICA riboside is in the range of 3–6 $\mu$g/ml. The data in Table 13 reflect diagnosis of MI by both ECG and CK-MB (as described above with respect to Table 12).

TABLE 13

INCIDENCE OF MI AND COMBINED CLINICAL OUTCOME BY PLASMA LEVEL OF AICA RIBOSIDE ($\mu$g/ml)

| AICA Riboside Plasma Level | Myocardial Infarction MI | Combined Clinical Outcome |
|---|---|---|
| <0.25 | n = 209 | n = 211 |
|  | 9 (4.3%) | 29 (13.7%) |
| 0.25–2.00 | n = 83 | n = 89 |
|  | 2 (2.4%) | 9 (10.1%) |
| 2.00–3.00 | n = 114 | n = 116 |
|  | 5 (4.4%) | 11 (9.5%) |
| 3.00–4.00 | n = 44 | n = 44 |
|  | 1 (2.3%) | 3 (6.8%) |
| 4.00–5.00 | n = 61 | n = 61 |
|  | 0 | 2 (3.3%) |
| 5.00–6.00 | n = 49 | n = 50 |
|  | 2 (4.1%) | 3 (6.0%) |
| >6.00 | n = 44 | n = 46 |
|  | 1 (2.3%) | 4 (8.7%) |

Other Embodiments

Other embodiments are within the following claims. In a preferred embodiment, the AICA riboside (or prodrug) is lyophilized to avoid variable discolorization. Pro-drugs may also be utilized, i.e., thoses which, when introduced to the body, are metabolized to the active forms of AICA riboside. AICA riborise prodrug compound comprise a modified AICA riboside and may have an AICA ribosyl moiety and at least one hydrocarbyloxycarbonyl or hydrocarbylcarbonyl moiety per equivalent weight of AICA ribosyl moiety. Such prodrugs of AICA riboside commonly exhibit one or more of the following improvements over AICA riboside, including: (1) more potent adenosine releasing effects; (2) increased half life; (3) increased brain penetration; (4) increased oral bioavailability; (5) increased myocardial targeting; and (6) in some cases, efficacy improvements over AICA riboside itself.

AICA riboside and prodrugs thereof ("AICA riboside compounds") can be administered in any standard manner using pharmaceutically acceptable buffers. To deliver AICA riboside compounds to patients, it is anticipated that they may be administered intravenously, by intracoronary or intraarterial infusion, by direct intramuscular injection, subcutaneously, orally, topically to the skin or mucous membranes, rectally or by inhalation. AICA riboside compounds may also be introduced into a patient's blood extracorporeally, for example, using a heart-lung machine or dialysis. Compounds acceptable for pharmaceutical use are well known.

Preferably, AICA riboside compounds are administered prophylactically. When such compounds are present in advance of an ischemic event, the net breakdown of ATP can be beneficially directed in larger measure to adenosine rather than inosine, and thus prevent tissue damage. If a drug is introduced into a patient to reach an ischemic region during or after an event causing ischemia, there is less ability to direct ATP to adenosine at that site because the target ATP pools are depleted relatively quickly. With a drug present as a prophylactic agent, there is also the possibility that the process sought to be interrupted can be slowed early enough to prevent the event or any permanent damage.

Other factors make it important to administer the drug before and/or during an ischemic event. If the drug is administered after blockage, it is less able to reach the tissue involved because there is little or no blood flow to the area, unless the ischemic area has undergone corrective reperfusion, such as by tPA administration, angioplasty or by-pass surgery. It is also believed that, for example, AICA riboside is metabolized to AICA ribotide and that this is one active form of the molecule. This metabolism is an energy-requiring reaction which utilizes ATP. If ATP is not available because of high metabolic activity and/or increased ATP destruction, then the AICA riboside cannot be made into this active form.

We claim:

1. A method of decreasing tissue damage associated with decreased blood flow in a patient at risk for tissue damage associated with decreased blood flow, which method comprises administering AICA riboside to said patient in an amount which provides a blood plasma concentration of said AICA riboside in said patient between 1 $\mu$g/ml and 20 $\mu$g/ml, for a sufficient time to reduce the risk of said tissue damage in said patient.

2. The method of claim 1 wherein said AICA riboside concentration is from about 3 $\mu$g/ml to about 6 $\mu$g/ml.

3. The method of claim 1 wherein said AICA riboside concentration is about 5 $\mu$g/ml.

4. The method of claim 1 wherein said blood plasma concentration of said AICA riboside is maintained by administering said AICA riboside in a dosage of from 0.01 mg/kg/min to 2.0 mg/kg/min.

5. The method of claim 4 wherein said AICA riboside dosage is from 0.05 mg/kg/min to 0.2 mg/kg/min.

6. The method according to claim 4 wherein AICA riboside dosage is about 0.1 mg/kg/min.

7. The method of claimed 4 wherein the duration of said administration is greater than four hours.

8. The method of claim 4 wherein the duration of said administration is about seven hours.

9. The method of claim 1 or 4 wherein said AICA riboside is administered intravenously.

10. The method of claim 1 wherein said AICA riboside is administered by adding to blood extracorporeally.

11. The method of claim 1 wherein said AICA riboside is administered by intracoronary infusion.

12. The method of claim 1 or 4 wherein AICA riboside is formed as a solution from a lyophilized AICA riboside.

13. The method of claim 1 or 4 wherein said tissue is cardiac muscle.

14. The method of claim 1 or 4 wherein said tissue damage occurs as a result of a heart attack.

15. The method of claim 1 or 4 wherein said tissue damage occurs as a result of a stroke.

16. A method of claim 1 or 4 wherein said administration occurs during surgery on said patient.

17. The method of claim 16 wherein said surgery is CABG surgery.

18. The method of claim 16 wherein said AICA riboside is administered before anesthesia of said patient, and continues for the duration of said surgery.

19. The method of claim 16 wherein said AICA riboside is administered before anesthesia of said patient and continues until at least about one hour following said surgery.

20. The method of claim 16 wherein said AICA riboside is administered before anesthesia of said patient and continues for about seven hours.

21. The method of claim 16 wherein said method further comprises providing a cardioplegic perfusate solution of said AICA riboside and perfusing the heart of said patient with said perfusate solution.

22. The method of claim 21 wherein the concentration of said AICA riboside in said perfusate solution is about 20 $\mu$M.

23. The method of claim 1, 2 or 4 wherein said method further comprises the step of identifying a human in need of prevention of said tissue damage caused by decreased blood flow prior to said administering of said AICA riboside.

24. A method of reducing the risk of tissue damage associated with decreased blood flow in a patient, which method comprises administering AICA riboside in a total dose of from 10 mg/kg to about 200 mg/kg.

25. The method of claim 24 wherein said total dose of AICA riboside is from about 30 mg/kg to about 160 mg/kg.

26. The method of claim 24 wherein said total dose of AICA riboside is about 40 mg/kg.

27. A method of decreasing tissue damage associated with decreased blood flow in a patient, which method comprises administering a prodrug of an AICA riboside to said patient in an amount effective to provide a blood plasma concentration of said AICA riboside between 1 $\mu$g/ml and 20 $\mu$g/ml in said patient, at least until the risk of said tissue damage in said patient is reduced.

28. The method of claim 27 wherein said prodrug is administered in an amount effective to provide a blood plasma concentration of AICA riboside in said patient of between about 3 $\mu$g/ml and about 6 $\mu$g/ml.

29. The method of claim 27 wherein said prodrug is administered in an amount effective to provide a blood plasma concentration of AICA riboside in said patient of about 5 $\mu$g/ml.

30. The method of claim 27 wherein said prodrug is administered orally.

31. The method of claim 1 or 4 wherein said AICA riboside is administered in combination with or in conjunction with allopurinol.

32. The method of claim 27 wherein said prodrug is administered in combination with or in conjunction with allopurinol.

33. The method of claim 31 wherein said allopurinol is administered in an amount of about 300 mg/day.

34. A method of reducing the risk of or reducing the severity of an adverse cardiovascular or cerebrovascular event in a human patient at risk for said adverse cardiovascular or cerebrovascular event, which method comprises administering to said patient in an amount of AICA riboside or a prodrug thereof which provides a blood plasma concentration of said AICA riboside in said patient of between 1 $\mu$g/ml and 20 $\mu$g/ml.

35. The method of claim 34 wherein said AICA riboside concentration is between about 3 $\mu$g/ml and about 6 $\mu$g/ml.

36. The method of claim 34 wherein said AICA riboside concentration is about 5 $\mu$g/ml.

37. The method of claim 34 wherein said blood plasma concentration of said AICA riboside is maintained by administering said AICA riboside in a dosage of from 0.01 mg/kg/min to 2.0 mg/kg/min.

38. The method of claim 34 wherein said AICA riboside dosage is from 0.05 mg/kg/min to 0.2 mg/kg/min.

39. The method according to claim 34 wherein AICA riboside dosage is about 0.1 mg/kg/min.

40. The method according to claim 34 wherein AICA riboside dosage is about 0.125 mg/kg/min.

41. The method of claim 34 or 37 wherein the duration of said administration is greater than four hours.

42. The method of claim 34 or 37 wherein the duration of said administration is about seven hours.

43. The method of claim 34 or 37 wherein AICA riboside is formed as a solution from a lyophilized AICA riboside.

44. The method of claim 34 or 37 wherein said adverse cardiovascular event is myocardial infarction.

45. The method of claim 34 or 37 wherein said adverse cerebrovascular event is a cerebrovascular accident.

46. A method of reducing the risk of or reducing the severity of an adverse cardiovascular or cerebrovascular event in a patient undergoing CABG surgery, which method comprises the steps of (a) administering to said patient about 0.1 mg/kg/min AICA riboside intravenously for about seven hours perioperatively; and (b) perfusing the heart of said patient with a perfusate solution of about 20 $\mu$M AICA riboside.

47. A method of reducing the risk of, or reducing the severity of cerebrovascular accident in a patient at risk for cerebrovascular accident, which method comprises administering AICA riboside to said patient in an amount of AICA riboside or prodrug thereof which provides a blood plasma concentration of AICA riboside in said patient of between about 3 $\mu$g/ml and about 6 $\mu$g/ml for a sufficient time to reduce the risk of cerebrovascular accident.

48. A method of reducing the risk of cardiac death in a patient at risk for cardiac death, which method comprises administering AICA riboside to said patient in an amount of AICA riboside or prodrug thereof which provides a blood plasma concentration of a AICA riboside in said patient of between about 3 $\mu$g/ml and about 6 micrograms/ml, for sufficient time to reduce the risk of said cardiac death.

49. A kit for use in administering AICA riboside to a patient undergoing cardiac surgery comprising:

a) lyophilized AICA riboside for use in preparing an AICA riboside solution for infusion into patient undergoing cardiac surgery; and b) AICA riboside in solution for use in preparing a cardioplegic perfusate solution to be used to perfuse the heart of a patient undergoing cardiac surgery.

50. A kit for use in administering AICA riboside to a patient comprising:

a) a sterile container of lyophilized non-pyrogenic AICA riboside.

51. A cardioplegic solution comprising AICA riboside in a concentration of about 20 $\mu$M.

52. The method of claim 32 wherein said allopurinol is administered in an amount of about 300 mg/day.

* * * * *